United States Patent
Hinton et al.

(10) Patent No.: US 11,385,218 B2
(45) Date of Patent: *Jul. 12, 2022

(54) MARKER COMPOSITIONS, AND METHODS FOR MAKING AND USING SAME

(71) Applicant: United Color Manufacturing, Inc., Newtown, PA (US)

(72) Inventors: Michael P. Hinton, Richboro, PA (US); Justin J. Frederico, Yardley, PA (US)

(73) Assignee: UNITED COLOR MANUFACTURING, INC., Newtown, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/683,425

(22) Filed: Nov. 14, 2019

(65) Prior Publication Data
US 2020/0080985 A1 Mar. 12, 2020

Related U.S. Application Data

(63) Continuation of application No. 15/685,108, filed on Aug. 24, 2017, now Pat. No. 10,509,020.
(Continued)

(51) Int. Cl.
*G01N 33/28* (2006.01)
*G01N 21/77* (2006.01)
(Continued)

(52) U.S. Cl.
CPC .......... *G01N 33/2882* (2013.01); *C10L 1/003* (2013.01); *C10L 1/02* (2013.01);
(Continued)

(58) Field of Classification Search
CPC ....... G01N 2030/045; G01N 2030/025; G01N 2030/8854; G01N 1/30; G01N 21/77;
(Continued)

(56) References Cited

U.S. PATENT DOCUMENTS 5,205,840 A   4/1993 Friswell
5,358,873 A   10/1994 Nowak
(Continued)

FOREIGN PATENT DOCUMENTS

KR  20020033033 A   5/2002
WO  2012125120 A1   9/2012
WO  2014179646 A1   11/2014

OTHER PUBLICATIONS

PCT International Search Report and Written Opinion, PCT/US2017/048320, dated Dec. 4, 2017, 14 pages.
(Continued)

*Primary Examiner* — Maureen Wallenhorst
(74) *Attorney, Agent, or Firm* — Quarles & Brady, LLP (57) ABSTRACT

The present disclosure provides compositions, methods, and systems for identifying marked hydrocarbon fluids. These compositions, methods, and systems utilize a gas chromatography marker including a pyrrolidinone. The methods and systems can identify the presence or absence of the gas chromatography marker and/or the pyrrolidinone. The compositions, methods, and systems can optionally utilize a spectroscopic marker.

16 Claims, 1 Drawing Sheet

Related U.S. Application Data (60) Provisional application No. 62/379,005, filed on Aug. 24, 2016.

(51) Int. Cl.
| | |
|---|---|
| *G01N 1/30* | (2006.01) |
| *G01N 30/72* | (2006.01) |
| *C10L 1/00* | (2006.01) |
| *C10L 1/02* | (2006.01) |
| *C10M 133/44* | (2006.01) |
| *C10M 171/00* | (2006.01) |
| *G01N 30/88* | (2006.01) |
| *C10N 30/20* | (2006.01) |
| *G01N 30/02* | (2006.01) |

(52) U.S. Cl.
CPC ........ *C10M 133/44* (2013.01); *C10M 171/00* (2013.01); *C10M 171/007* (2013.01); *G01N 1/30* (2013.01); *G01N 21/77* (2013.01); *G01N 30/72* (2013.01); *C10N 2030/20* (2013.01); *G01N 2030/025* (2013.01); *G01N 2030/8854* (2013.01); *Y10T 436/13* (2015.01); *Y10T 436/21* (2015.01)

(58) Field of Classification Search
CPC .... G01N 33/28; G01N 33/2882; G01N 30/72; Y10T 436/13; Y10T 436/145555; Y10T 436/17; Y10T 436/21; C10L 1/003; C10L 1/02; C10M 133/44; C10M 171/00; C10M 171/007; C01N 2230/20
USPC ..... 436/56, 60, 96, 106, 139, 161, 164, 171; 422/89, 82.05, 82.09
See application file for complete search history.

(56) References Cited

U.S. PATENT DOCUMENTS

| | | |
|---|---|---|
| 5,490,872 A | 2/1996 | Friswell |
| 5,498,808 A | 3/1996 | Smith |
| 5,672,182 A | 9/1997 | Smith |
| 5,676,708 A | 10/1997 | Smith |
| 5,723,338 A | 3/1998 | Rutledge |
| 5,858,930 A | 1/1999 | Desai |
| 6,002,056 A | 12/1999 | Smith |
| 6,482,651 B1 | 11/2002 | Smith |
| 6,514,917 B1 | 2/2003 | Smith |
| 7,157,563 B2 | 1/2007 | Smith |
| 7,163,827 B2 | 1/2007 | Smith |
| 7,825,159 B2 | 11/2010 | Frederico |
| 9,759,697 B2 | 9/2017 | Gras |
| 10,509,020 B2 * | 12/2019 | Hinton ............... G01N 33/2882 |
| 10,774,280 B2 * | 9/2020 | Doshi ..................... C10L 1/226 |
| 2007/0184555 A1 | 8/2007 | Banavali |
| 2014/0004615 A1 | 1/2014 | Wilkinson |
| 2016/0187314 A1* | 6/2016 | Blumenfeld ....... G01N 33/2882 506/4 |

OTHER PUBLICATIONS

Stephens, R. Analytical Chemistry, vol. 56, No. 9, Aug. 1984, pp. 1608-1610.

* cited by examiner

Fig. 1

MARKER COMPOSITIONS, AND METHODS FOR MAKING AND USING SAME

CROSS-REFERENCE TO RELATED APPLICATIONS

This application is a continuation of U.S. patent application Ser. No. 15/685,108 filed Aug. 24, 2017, now U.S. Pat. No. 10,509,020, which claims the benefit of U.S. Provisional Patent Application Ser. No. 62/379,005 filed on Aug. 24, 2016 and entitled "Marker Compositions, and Methods for Making and Using Same", the entire contents of which is hereby incorporated by reference.

STATEMENT REGARDING FEDERALLY SPONSORED RESEARCH n/a

BACKGROUND OF THE INVENTION

The field of the invention is marker compositions for fluids. More particularly, the invention relates to multi-layered marker compositions.

A marker is a substance which can be used to tag products, typically petroleum products, as well as alcohols and a number of other suitable fluids, for subsequent detection. The marker is normally dissolved in a fluid to be identified, then subsequently detected by performing a physical or chemical test on the tagged fluid. For example, markers are sometimes used by government authorities to ensure that the appropriate tax has been paid on particular grades of fuel. Oil companies also mark their products to help identify those who have diluted or altered their products. These companies often go to great expense to make sure their branded petroleum products meet certain specifications regarding volatility and octane number, for example, as well as to provide their petroleum products with effective additive packages containing detergents and other components. Consumers rely upon the product names and quality designations to assure that the product being purchased is the quality desired.

It is possible for unscrupulous persons to increase profits by selling an inferior product at the price consumers are willing to pay for a high quality branded or designated product. Higher profits can also be made simply by diluting the branded product with an inferior product. Policing retailers/dealers, for example, who substitute one product for another or blend branded products with inferior products is difficult in the case of gasoline because the blended products will qualitatively display the presence of each component in the branded products. The key ingredients of the branded products are generally present in such low levels that quantitative analysis to detect dilution with an inferior product is very difficult, time consuming and expensive.

Marker systems for petroleum products, including, but not limited to, fuels, lubes, greases, etc., have been suggested but various drawbacks have existed which have hindered their effectiveness. Many currently available markers cannot be used as both forensic markers, detected by, but not limited to analysis by Gas Chromatography (GC), and simple field test markers detected by, but not limited to, development or extraction of the marker. Many known markers are easily removed from the fluid to which they are added destroying the integrity of the marker system. Many currently available markers cannot be easily combined to detect marker product with a component that cannot be laundered from the fuel. And current methods of lab analysis of these markers ends to be very expensive.

In view of the above, it would be desirable to provide a composition useful as a marker and that could be detected not only in the field, but also in the lab. It would be desirable to combine field test technology with existing chromatography techniques to provide not only field test results but also a laboratory confirmation of the marker presence, using common lab techniques, such as, but not limited to, analysis by GC. Additionally, the marker should be able to accomplish the above and remain resistant to undesired extraction or removal (laundering) by unscrupulous persons. Additionally it would be desirable to provide a marker composition that could be used in a wide variety of fluids, including, but not limited to, petroleum products, alcohols, etc. Petroleum products may include, but are not limited to, fuels, lubes, greases, etc. It would also be desirable to provide economical detection methods not requiring advanced training of the operator.

SUMMARY OF THE INVENTION

In an aspect, the present disclosure provides a method of identifying marked hydrocarbon fluids that have been laundered, wherein unlaundered marked hydrocarbon fluids contain a gas chromatography marker and a spectroscopic marker. The gas chromatography marker includes a pyrrolidinone. The method includes: a) introducing a first portion of a hydrocarbon fluid sample that is suspecting of having been laundered into a gas chromatography system, thereby resulting in a gas chromatography report of the hydrocarbon fluid sample; b) spectroscopically analyzing a second portion of the hydrocarbon fluid sample, thereby resulting in a spectroscopic report of the hydrocarbon fluid sample; c) identifying the presence or absence of the gas chromatography marker using the gas chromatography report and identifying the presence or absence of the spectroscopic marker using the spectroscopic report; and d) based on the identifying of step c): if the gas chromatography marker and the spectroscopic marker are identified as present, then indicating that the hydrocarbon fluid sample is marked and unlaundered; if the gas chromatography marker is identified as present and the spectroscopic marker is identified as absent, then indicating that the hydrocarbon fluid sample is marked and laundered; and if the gas chromatography marker and the spectroscopic marker are identified as absent, then indicating the hydrocarbon fluid is unmarked.

In another aspect, the present disclosure provides a method of marking a subset of hydrocarbon fluids in circulation within a market and detecting presence of the marking. The method includes: a) adding a gas chromatography marker comprising a pyrrolidinone to the subset of the hydrocarbon fluids in circulation within the market; b) selecting a sample of one of the hydrocarbon fluids in circulation within the market; c) introducing at least a portion of the sample of one of the hydrocarbon fluids in circulation within the market into a gas chromatography system, thereby resulting in a gas chromatography report of the sample; and d) identifying the presence or absence of the pyrrolidinone in the sample using the gas chromatography report, thereby identifying whether the sample is from within or without the subset of hydrocarbon fluids.

In a further aspect, the present disclosure provides a method of identifying a hydrocarbon fluid containing a gas chromatography marker including a pyrrolidinone. The method includes: a) introducing a sample of the hydrocarbon fluid into a gas chromatography system, thereby resulting in a gas chromatography report of the sample; and b) identifying the presence of the pyrrolidinone in the hydrocarbon fluid using the gas chromatography report.

In yet another aspect, the present disclosure provides a marker composition. The marker composition includes: a gas chromatography marker including a pyrrolidinone; and a solvent. The pyrrolidinone is a 1-alkyl-2-pyrrolidinone or a 1-alkenyl-2-pyrrolidinone, the 1-alkyl-2-pyrrolidinone including a non-cyclic alkyl group having between 3 and 7 carbon atoms, between 9 and 11 carbon atoms, or between 13 and 24 carbon atoms or a cycloalkyl group having between 4 and 24 carbon atoms, the 1-alkenyl-2-pyrrolidinone including an alkenyl group having between 2 and 24 carbon atoms.

In yet a further aspect, the present disclosure provide a marker composition. The marker composition includes: a gas chromatography marker including a pyrrolidinone; and a spectroscopic marker. The pyrrolidinone is a 1-alkyl-2-pyrrolidinone or a 1-alkenyl-2-pyrrolidinone, the 1-alkyl-2-pyrrolidinone including a non-cyclic alkyl group having between 3 and 7 carbon atoms, between 9 and 11 carbon atoms, or between 13 and 24 carbon atoms or a cycloalkyl group having between 4 and 24 carbon atoms, the 1-alkenyl-2-pyrrolidinone including an alkenyl group having between 2 and 24 carbon atoms.

In an additional aspect, the present disclosure provides a marked hydrocarbon fluid. The marked hydrocarbon fluid includes a hydrocarbon fluid and the marker compositions as described herein. The marker composition is present in an amount sufficient to provide a concentration of the pyrrolidinone in the marker hydrocarbon fluid of between 0.1 ppm and 500 ppm, to provide a concentration of the spectroscopic marker in the marker hydrocarbon fluid of between 0.1 ppm and 500 ppm, or a combination thereof.

In yet another aspect, the present disclosure provides a kit. The kit includes the marker composition as described herein and a reference gas chromatography report for the pyrrolidinone of the marker composition.

In yet a further aspect, the present disclosure provides a system for identifying hydrocarbon fluids marked with a gas chromatography marker including a pyrrolidinone. The system includes a gas chromatography with nitrogen phosphorus detector (GC-NPD) system; and a computer. The computer has a processor and a memory. The memory has stored thereon a reference gas chromatography report for the pyrrolidinone and instructions that, when executed by the processor, cause the processor to receive a gas chromatography report from the GC-NPD system and identify the present or absence of the gas chromatography marker based on a comparison with the reference gas chromatography report.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

In order to assist the understanding of this invention, reference will now be made to the appended drawings, in which like reference characters refer to like elements. The drawings are exemplary only, and should not be construed as limiting the invention.

DETAILED DESCRIPTION OF THE INVENTION

Before the present materials and methods are described, it is understood that this disclosure is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

As used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

It should be apparent to those skilled in the art that many additional modifications beside those already described are possible without departing from the inventive concepts. In interpreting this disclosure, all terms should be interpreted in the broadest possible manner consistent with the context. Variations of the term "comprising", "including", or "having" should be interpreted as referring to elements, components, or steps in anon-exclusive manner, so the referenced elements, components, or steps may be combined with other elements, components, or steps that are not expressly referenced. Embodiments referenced as "comprising", "including", or "having" certain elements are also contemplated as "consisting essentially of" and "consisting of" those elements, unless the context clearly dictates otherwise. It should be appreciated that aspects of the disclosure that are described with respect to a system are applicable to the methods, and vice versa, unless the context explicitly dictates otherwise.

Numeric ranges disclosed herein are inclusive of their endpoints. For example, a numeric range of between 1 and 10 includes the values 1 and 10. When a series of numeric ranges are disclosed for a given value, the present disclosure expressly contemplates ranges including all combinations of the upper and lower bounds of those ranges. For example, a numeric range of between 1 and 10 or between 2 and 9 is intended to include the numeric ranges of between 1 and 9 and between 2 and 10.

Unless defined otherwise, all technical and scientific terms and abbreviations used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein, including, but not limited to, U.S. Pat. Nos. 5,498,808, 5,676,708, 5,672,182, 5,858,930, 6,002,056, 6,482,651, 7,157,563, 7,163,827 and 7,825,159 are incorporated by reference for all purposes including describing and disclosing the chemicals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

As used herein, an "alkyl group" refers to an alkane lacking a single hydrogen and includes straight chain, branched, and cyclic alkyl groups. For clarity, as used herein, an alkyl group with three carbon atoms includes isopropyl groups, unless the context clearly dictates otherwise, and the same is true for other alkyl groups. Similarly, an alkyl group with six carbon atoms includes cyclohexyl groups, unless the context clearly dictates otherwise. When defining the number of carbon atoms in an alkyl group, all branches are considered. So, an isopropyl group is an alkyl group having three carbon atoms.

As used herein, an "alkenyl group" refers to an alkene lacking a single hydrogen and includes straight chain, branched, and cyclic alkenyl groups.

As used herein, "comprising" is an inclusive term and includes recited components or method steps and other non-recited components or method steps.

As used herein, "consisting essentially of" shall have the definition used in patent prosecution before the United States Patent and Trademark Office as of the filing date of this application. A description or claim described as consisting essentially of certain components or method steps shall be limited in scope to the recited components or method steps and those that do not materially affect the basic and novel characteristic(s) of the described or claimed invention.

As used herein, "consisting of" is an exclusive term and includes only recited components or method steps, excluding other non-recited components or method steps.

As used herein, a "cycloalkyl group" refers to a cycloalkane lacking a single hydrogen and includes unsubstituted cycloalkyl groups and cycloalkyl groups having one or more alkyl group substitutions. Multiple rings can be present in a single cycloalkyl group, including fused rings.

As used herein, a "gas chromatography marker" refers to a chemical entity that can be detected by a gas chromatographic means, including but not limited to, gas-chromatography with nitrogen phosphorus detector, gas chromatography-mass spectrometry, and other similar gas chromatographic methods known to those having ordinary skill in the art.

As used herein, a "gas chromatography with nitrogen phosphorus detector marker" refers to a chemical entity that can be detected by gas chromatography with nitrogen phosphorus detector.

As used herein, a "non-cyclic alkyl group" refers to an alkyl group that includes no cyclic rings.

As used herein, a "non-pyrrolidinone" refers to a compound excluding a pyrrolidinone group (also sometimes referred to as a pyrrolidone group).

As used herein, a "phthalein" refers to a compound formed by a reaction of phthalic anhydride with a phenol.

As used herein, a "pyrrolidinone" refers to a compound including a pyrrolidinone group (also sometimes referred to as a pyrrolidone group).

As used herein, a "nonaqueous" composition refers to a composition where water is present in an amount of less than 1% by weight.

As used herein, the term "red dye" refers to a dye having a visible electromagnetic radiation absorption maximum of between 500 nm and 580 nm.

As used herein, a "spectroscopic marker" refers to a chemical entity that can be detected by spectroscopic means, including but not limited to, fluorescence spectroscopy, absorbance spectroscopy, Raman spectroscopy, near-infrared spectroscopy, and other spectroscopic methods known to those having ordinary skill in the spectroscopic arts. It should be appreciated that while a spectroscopic marker refers to a chemical entity that can be detected by spectroscopic means, the present disclosure is not limited to actually detecting the spectroscopic marker by such means. For example, a spectroscopic marker can be detected by chromatographic means in ways understood to those having ordinary skill in the analytical chemistry arts.

As used herein, the term "yellow dye" refers to a dye having a visible electromagnetic radiation absorption maximum of between 400 nm and 475 nm.

Abbreviations

AFID—Alkali Flame Ionization Detector
ECD—Electron Capture Detector
FID—Flame Ionization Detector
GC—Gas Chromatography
GC-MS—Gas Chromatograpy-Mass Spectrometry
GC-NPD—Gas Chromatography with Nitrogen Phosphorus Detector
GLP—Gel Liquid Permeation
HECD—Hall Electrolytic Conductivity Detector
LC—Liquid Chromatography
LC-MS—Liquid Chromatography-Mass Spectrometry
MS—Mass Spectrometry
NIR—Near Infrared
PID—Photoionization Detector
UV-Vis—Ultraviolet-Visible This disclosure is directed to multilayered marker compositions that substantially solve the problem of the launderability, or removal, of spectroscopic markers from organic solvents, including but not limited to, petroleum products, lubricants, or any other hydrocarbon fluids, by introducing a multilayered marker composition reducing one's ability to substantially remove, or launder, the composition from the marked fluid easily or in an economical manner. The novel and nonobvious multilayered marker compositions disclosed herein combine the ability to not only conduct simple field tests to determine the presence of the composition in the marked fluid, but also enable more sophisticated laboratory analysis to detect the composition in the marked fluid.

The present disclosure provides a marker composition for marking a hydrocarbon fluid. The marker composition can take a variety of forms, which can be combined as understood by those having ordinary skill in the art.

In some cases, the marker composition can include a gas chromatography (GC) marker. In some cases, the marker composition can consist essentially of the GC marker. In some cases, the marker composition can consist of the GC marker.

In some cases, the marker composition can include the GC marker and a solvent. In some cases, the marker composition can consist essentially of the GC marker and the solvent. In some cases, the marker composition can consist of the GC marker and the solvent. In each of these compositions, the GC marker can be present in an amount by weight of between 1% and 99%, between 25% and 75%, or between 40% and 60%. In each of these compositions, the solvent can be present in an amount by weight of between 1% and 99%, between 25% and 75%, or between 40% and 60%.

In some cases, the marker composition can include the GC marker and a spectroscopic marker. In some cases, the marker composition can consist essentially of the GC marker and the spectroscopic marker. In some cases, the marker composition can consist of the GC marker and the spectroscopic marker. In each of these compositions, the GC marker can be present in an amount by weight of between 1% and 99%, between 25% and 75%, or between 40% and 60%. In each of these compositions, the spectroscopic marker can be present in an amount by weight of between 1% and 99%, between 25% and 75%, or between 40% and 60%.

In some cases, the marker composition can include the GC marker, the spectroscopic marker, and the solvent. In some cases, the marker composition can consist essentially of the GC marker, the spectroscopic marker, and the solvent. In some cases, the marker composition can consist of the GC marker, the spectroscopic marker, and the solvent. In each of these compositions, the GC marker can be present in an amount by weight of between 10% and 85%, between 20% and 70%, or between 25% and 60%. In each of these compositions, the spectroscopic marker can be present in an amount by weight of between 5% and 80%, between 10% and 50%, or between 15% and 25%. In each of these compositions, the solvent can be present in an amount by weight of between 10% and 85%, between 20% and 70%, or between 25% and 60%.

Any of the aforementioned marker compositions can be nonaqueous.

The GC marker in any of the aforementioned marker compositions can be a gas chromatography with nitrogen phosphorus detector (GC-NPD) marker.

The gas chromatography marker in any of the aforementioned marker compositions can include a pyrrolidinone. The gas chromatography marker in any of the aforementioned marker compositions can consist essentially of a pyrrolidinone. The gas chromatography marker in any of the aforementioned marker compositions can consist of a pyrrolidinone.

In some cases, the pyrrolidinone can be any pyrrolidinone that is soluble in a hydrocarbon fluid at levels from 0.01 ppm to 500 ppm.

In certain applications, 1-alkyl-2-pyrrolidinones, where the alkyl group is of any length, can be useful as gas chromatography markers, including GC-NPD markers.

In certain applications, it can be beneficial to utilize pyrrolidinones having a higher molecular weight and/or having a larger alkyl substitution. In these applications, the pyrrolidinone can be an 1-alkyl-2-pyrrolidinone, wherein the alkyl group is an alkyl group having 3 or more carbon atoms, including but not limited to, an alkyl group having between 3 and 40 carbon atoms, an alkyl group having between 4 and 30 carbon atoms, an alkyl group having between 5 and 20 carbon atoms, an alkyl group having between 6 and 18 carbon atoms, an alkyl group having between 8 and 16 carbon atoms, or an alkyl group having between 6 and 12 carbon atoms.

In certain applications, it can be beneficial for the pyrrolidinone to be a 1-alkyl-2-pyrrolidinone, wherein the alkyl group is an alkyl group having 3 carbon atoms, 4 carbon atoms, 5 carbon atoms, 6 carbon atoms, or 7 carbon atoms.

In certain applications, it can be beneficial for the pyrrolidinone to be a 1-alkyl-2-pyrrolidinone, wherein the alkyl group is an alkyl group having 9 carbon atoms, 10 carbon atoms, 11 carbon atoms, 12 carbon atoms, 13 carbon atoms, 14 carbon atoms, 15 carbon atoms, 16 carbon atoms, 17 carbon atoms, 18 carbon atoms, 19 carbon atoms, 20 carbon atoms, 21 carbon atoms, 22 carbon atoms, 23 carbon atoms, or 24 carbon atoms.

In certain applications, 1-cycloalkyl-2-pyrrolidinones, where the cycloalkyl group is of any length, can be useful as gas chromatography markers, including GC-NPD markers.

In certain applications, 1-alkenyl-2-pyrrolidinones, where the alkenyl group is of any length, can be useful as GC markers, including GC-NPD markers.

In certain applications, it can be beneficial to utilize a pyrrolidinone selected from the group consisting of 1-methyl-2-pyrrolidinone, 1-ethyl-2-pyrrolidinone, 1-cyclohexyl-2-pyrrolidinone, 1-octyl-2-pyrrolidinone, 1-dodecyl-2-pyrrolidinone, 1-octadecyl-2-pyrrolidinone, and 1-vinyl-2-pyrrolidinone.

In certain applications, it can be beneficial to utilize a pyrrolidinone selected from the group consisting of 1-cyclohexyl-2-pyrrolidinone, 1-octadecyl-2-pyrrolidinone, and 1-vinyl-2-pyrrolidinone.

In some cases, the gas chromatography marker or the GC-NPD marker can be a non-pyrrolidinone compound, such as pyrolines, piperidones, pipirizines, pyrolines, pyridazones, imidazolidones, oxazoles, oxazolines, and oxazolidines.

The spectroscopic marker in any of the aforementioned compositions including any spectroscopic markers known to have a reproducible spectroscopic signal that is distinguishable from inherent spectroscopic signals related to the hydrocarbon fluid being marked. For example, the spectroscopic marker can be a dye that has an absorption spectrum that is distinguishable from the hydrocarbon fluid being marked. As another example, the spectroscopic marker can be a fluorescent dye that has a fluorescence spectrum that is distinguishable from the hydrocarbon fluid being marked.

In some cases, the spectroscopic marker can be any spectroscopic marker that is soluble in a hydrocarbon fluid at levels from 0.01 ppm to 500 ppm.

In certain applications, the spectroscopic marker can be a red dye or a yellow dye. The spectroscopic marker can be Solvent Red 164 or Solvent Yellow 124.

In certain applications, the spectroscopic marker is:

(I)

wherein $Ar^1$ and $Ar^2$ each independently represent a substituted or unsubstituted phenylene group or a substituted or unsubstituted naphthylene group; $R^1$ represents a straight or branched chain alkyl group having 1 to 22 carbon atoms; $R^2$ represents a hydrogen atom or a group of the formula $C(O)R^4$ where $R^4$ is a hydrogen atom or a straight or branched chain alkyl group having 1 to 22 carbon atoms; $R^3$ represents a hydrogen atom, a straight or branched chain alkyl group having 1 to 12 carbon atoms, a straight or branched chain alkoxy group having 1 to 12 carbon atoms, a hydroxyl group, a substituted or unsubstituted phenyl group or a substituted or unsubstituted naphthyl group; and Z represents a hydrogen atom or a group of atoms that combine with $Ar^2$ or $R^3$ to form a lactone ring.

In certain applications, the spectroscopic marker can be a phthalein. The spectroscopic marker can be a phthalein dibutyrate. The spectroscopic marker can be a phthalein ester. The spectroscopic marker can be selected from the group consisting of fluoroscein dibutyrate, cresolphthalein, o-cresolphthalein dibutyrate, and thymolphthalein. The spectroscopic marker can be selected from the group consisting of cresolphthalein dibutyrate ester, cresolphthalein monobutyrate ester, cresolphthalein diisopropylate ester, cresolphthalein di-n-propylate ester, cresolphthalein dihexanoate ester, cresolphthalein dipentanoate ester, and cresolphthalein dilaurate ester. The spectroscopic marker can be selected from the group consisting of naphtholphthalein dibutyrate ester, thymolphthalein dibutyrate ester, and thymolphthalein dipropanoate ester. The spectroscopic marker can be selected from the group consisting of sec-butylphenolphthalein dibutyrate ester and di-sec-butylphenolphthalein dibutyrate ester.

In some cases, the solvent can be a polar solvent. In some cases, the solvent can be an aprotic solvent. In some cases, the solvent can be selected from the group consisting of petroleum naphtha (boiling points from 100° F. to 250° F.); alcohols, including methanol, ethanol. propanol, butanol, and the like; glycol ethers, including ethylene glycol phenylethyl ether, ethylene glycol dimethyl ether, ethylene glycol diethyl ether, ethylene glycol diphenyl ether, and the like; dimethyl formamide; dimethyl sulfoxide; xylene; toluene; acetone; ethyl acetate; a petroleum product, including gasoline, kerosene, diesel fuel, jet fuel, and the like; and combinations thereof.

The present disclosure also provides marked hydrocarbon fluids. In some cases, the marked hydrocarbon fluids comprise a hydrocarbon fluid and one or more of the marker compositions described elsewhere herein. In some cases, the marked hydrocarbon fluids consist essentially of a hydrocarbon fluid and one or more of the marker compositions described elsewhere herein. In some cases, the marked hydrocarbon fluids consist of a hydrocarbon fluid and one or more of the marker compositions described elsewhere herein.

In each of the marked hydrocarbon fluids, the marker composition can be present in an amount sufficient to provide a concentration of pyrrolidinone in the marked hydrocarbon fluid of between 0.1 ppm and 500 ppm, including but not limited to, a concentration of between 0.5 ppm and 100 ppm, between 1 ppm and 50 ppm, or between 5 ppm and 25 ppm. In some cases, where a spectroscopic marker is present, the marker composition can be present in an amount sufficient to provide a concentration of spectroscopic marker in the marked hydrocarbon fluid of between 0.1 ppm and 500 ppm, including but not limited to, a concentration of between 0.5 ppm and 100 ppm, between 1 ppm and 50 ppm, or between 5 ppm and 25 ppm.

The present disclosure also provides kits. The kits can include any of the marker compositions described herein and information regarding the GC properties and/or the spectroscopic properties of the marker composition. The information can include a reference GC report for the pyrrolidinone. In cases where a spectroscopic marker is present, the information can include a reference spectroscopic report for the spectroscopic marker.

Markers are used in petroleum products such as liquid hydrocarbons, gasoline, diesel fuel, solvents, lubricants, brake fluid, hydraulic fluid, gasohol, kerosene, jet fuel, heating oil, bunker fuels, and other fluids as a means of ensuring product & brand integrity by providing a means to detect adulterated product. Typical adulteration scenarios include the substitution of the premium product with one of lesser quality or the commingling of the premium product with a lesser grade. Other scenarios include the misuse of subsidized or lower taxed fuels.

Phthaleins are described that function well as markers for fuels and lubricants. These markers are added at 0.5 to 50 ppm levels and enable satisfactory quantitative testing. Products containing phthaleins are difficult to prepare as concentrated solutions because of limited solubility, and they are difficult to dissolve into petroleum products. These problems are solved using strong co-solvents. By way of example only, polar-aprotic solvents like 1-octylpyrrolidinone, a.k.a. n-ocytylpyrrolidinone, (NOP) are well suited for this as the phthaleins are very soluble in the NOP, and in turn the NOP is soluble in the petroleum product. The commercial products marketed to the end users are formulated as mixtures of the actual phthalein, NOP, and solvent. The pyrrolidinone provides not only improved solubility to the phthalein resulting in a stable formulation of both components but also an improved dispersibility of the phthalein into the fuel or other fluid.

For example, these phthalein compositions are therefore prepared as mixtures of NOP, phthalein, and solvent. It was found that the resulting compositions according to embodiments of the present disclosure exhibited surprising and unexpected results, compared to the spectroscopic markers individually. The novel and non-obvious compositions herein disclosed result in a composition that is not only difficult to launder, but also may be tested in the field and in the lab to determine if the fuel/fluid has been adulterated.

In addition to the use of phthalein-based spectroscopic markers, many other types of markers may be used in embodiments of the disclosed compositions. Phthalein-based (including other chemical based markers) include, but are not limited to, fluoroscein dibutyrate, cresolphthaleine, o-Cresol phthalein dibutyrate, thymolphthalein, and any other suitable markers. Spectroscopic markers may include, but not limited to, naphtholphthalein dibutyrate ester, thymolphthalein dibutyrate ester, thymolphthalein dipropanoate ester, cresolphthalein dibutyrate ester, cresolphthalein monobutyrate ester, cresolphthalein diisopropylate ester, cresolphthalein di-n-propylate ester, cresolphthalein dihexanoate ester, cresolphthalein dipentanoate ester, cresolphthalein dilaurate ester, sec-buytlphenolphthalein dibutyrate ester and di-sec-butylphenolphthalein dibutyrate ester. For example the spectroscopic marker may be comprised of the compound according to the formula:

(I)

wherein $Ar^1$ and $Ar^2$ each independently represent a substituted or unsubstituted phenylene group or a substituted or unsubstituted naphthylene group; $R^1$ represents a straight or branched chain alkyl group having 1 to 22 carbon atoms; $R^2$ represents a hydrogen atom or a group of the formula $C(O)R^4$ where $R^4$ is a hydrogen atom or a straight or branched chain alkyl group having 1 to 22 carbon atoms; $R^3$ represents a hydrogen atom, a straight or branched chain alkyl group having 1 to 12 carbon atoms, a straight or branched chain alkoxy group having 1 to 12 carbon atoms, a hydroxyl group, a substituted or unsubstituted phenyl group or a substituted or unsubstituted naphthyl group; and Z represents a hydrogen atom or a group of atoms that combine with $Ar^2$ or $R^3$ to form a lactone ring.

It is envisioned that many non-phthalein spectroscopic markers may be used in embodiments of the disclosed compositions. In addition, spectroscopic markers described in U.S. Pat. Nos. 5,498,808, 5,676,708, 5,672,182, 5,858,930, 6,002,056, 6,482,651, 7,157,563, 7,163,827 and 7,825,159 are incorporated herein by reference for all purposes.

In order to adulterate fuels and other fluids containing a spectroscopic marker, routinely the first step is an attempt to remove the marker. This process is commonly known as laundering. Laundering is accomplished using a variety of techniques including: treatment of the marked fuel with acids or bases; bleaching agents; and/or filtration through materials such as clay or charcoal. Filtration is especially common as it does not use harmful chemicals that would otherwise destroy the performance of the fuel or other fluid and/or change the properties of the fuel or other fluid. Markers that are easily laundered fail to protect the fuel/fluid thus allowing it to be used in an unintended manner.

It is demonstrated that pyrrolidinones cannot be completely removed, even by the most sophisticated of techniques. Thus if both a spectroscopic marker and pyrrolidinone are formulated quantitatively to provide known concentrations in the fuel, fuel additive, or other fluid according to an embodiment of this disclosure, and therefore the fluid to which they are to be added, even in cases where persons have removed the phthalein component of the marker, sufficient amounts, if not all, of the pyrrolidinone remains and can be detected using a GC test method. This GC method can use a nitrogen detector to provide the sensitivity and resolution necessary to see low ppm concentrations of the NOP. Normal FID and MS detection are not sufficient to achieve the results necessary to detect the NOP from the fuel/fluid components in a cost effective testing procedure.

Compositions according to this disclosure can therefore be prepared that can undergo both quantitative chemical testing with standard alkali reagents providing the development and extractant test results for these phthalein markers, and in addition a quantitative determination of the pyrrolidinone by GC may be performed as both a forensic conformation of the marker in the fluid and as proof that laundering occurred.

This disclosure provides a method of identifying a hydrocarbon fluid comprising a gas chromatography marker. The method includes: a) introducing a sample of the hydrocarbon fluid into a gas chromatography system, thereby resulting in a gas chromatography report of the sample; and b) identifying the presence of the pyrrolidinone in the hydrocarbon fluid using the gas chromatography report. In some cases, the hydrocarbon fluid can further comprise a spectroscopic marker. In these cases, the method can further include: c) spectroscopically analyzing a second sample of the hydrocarbon fluid, thereby resulting in a spectroscopic report of the second sample; and d) identifying the presence of the spectroscopic marker in the hydrocarbon fluid using the spectroscopic report.

This disclosure also provides a method of marking a subset of hydrocarbon fluids in circulation within a market and detecting the presence of the marking. The method includes: a) adding a gas chromatography marker comprising a pyrrolidinone to the subset of the hydrocarbon fluids in circulation within the market; b) selecting a sample of one of the hydrocarbon fluids in circulation within the market; c) introducing the sample of one of the hydrocarbon fluids in circulation within the market into a gas chromatography system, thereby resulting in a gas chromatography report of the sample; and d) identifying the presence or absence of the pyrrolidinone in the sample using the gas chromatography report, thereby identifying whether the sample is from within or without the subset of hydrocarbon fluids. The adding of step a) can include adding the GC marker in an amount necessary to provide the pyrrolidinone in the subset of the hydrocarbon fluids in an amount of between 0.1 ppm and 500 ppm, including but not limited to, any other GC marker or pyrrolidinone concentration ranges disclosed herein. This method can include any of the features described above with respect to the method of identifying a hydrocarbon fluid containing a gas chromatography marker. In some cases, the method can further include: e) adding a spectroscopic marker to the subset of the hydrocarbon fluids in circulation within the market; f) spectroscopically analyzing at least a second portion of the sample of one of the hydrocarbon fluids in circulation within the market, thereby resulting in a spectroscopic report of the sample; and g) identifying the presence or absence of the spectroscopic marker in the sample using the spectroscopic report, thereby identifying whether the sample is from within or without the subset of hydrocarbon fluids. The adding of step e) can include adding the spectroscopic marker marker in an amount necessary to provide the spectroscopic marker in the subset of the hydrocarbon fluids in an amount of between 0.1 ppm and 500 ppm, including but not limited to, any other spectroscopic marker concentration ranges disclosed herein.

This disclosure also provides a method of identifying marked hydrocarbon fluids that have been laundered, wherein unlaundered marked hydrocarbon fluids contain a gas chromatography marker and a spectroscopic marker. The method includes: a) introducing a first portion of a hydrocarbon fluid sample that is suspecting of having been laundered into a gas chromatography system, thereby resulting in a gas chromatography report of the hydrocarbon fluid sample; b) spectroscopically analyzing a second portion of the hydrocarbon fluid sample, thereby resulting in a spectroscopic report of the hydrocarbon fluid sample; c) identifying the presence or absence of the gas chromatography marker using the gas chromatography report and identifying the presence or absence of the spectroscopic marker using the spectroscopic report; and d) based on the identifying of step c): if the gas chromatography marker and the spectroscopic marker are identified as present, then indicate that the hydrocarbon fluid sample is marked and unlaundered; if the gas chromatography marker is identified as present and the spectroscopic marker is identified as absent, then indicate that the hydrocarbon fluid sample is marked and laundered; and if the gas chromatography marker and the spectroscopic marker are identified as absent, then indicate the hydrocarbon fluid is unmarked.

In each of these methods, the introducing of a sample or portion of a fluid into a GC system step can include introducing the sample or portion of a fluid into a GC-NPD system, thereby resulting in a GC-NPD report. The GC-NPD system can include a flame thermionic detector or an alkali flame ionization detector. In these cases, the GC report resulting from the introducing step can include an intensity value that is proportional to an amount of nitrogen or phosphorus in the sample or fluid. This intensity can be time-variable as a function of elution times of the various components of the sample or fluid.

In each of these methods, in some cases, the introducing of a sample or portion of a fluid into a GC system step can include introducing the sample or portion of a fluid into a GC-MS system, a GC-NPD system, including a GC-NPD system with a flame thermionic detector (FTD) or an alkali-flame ionization detector (AFID), a GC-Hall electrolytic conductivity detector (HECD) system, a GC-flame ionization detector (FID) system, a GC-electron capture detector (ECD) system, a GC-photionization detector (PID) system, or a combination thereof.

The introducing of a sample or portion of a fluid into the GC system step can also include use of a fused silica column, a polyethylene glycol column, a cyano propyl column, a trifluorpropyl column, a substituted polysiloxane column, or the like. The introducing of a sample or portion of a fluid into the GC system step can include use of a carrier gas selected from the group consisting of nitrogen, helium, and combinations thereof. Other operational parameters of the gas chromatography system can be optimized in ways understood to those having ordinary skill in the art for the purpose of improving separation between the GC marker and the various components of the marked hydrocarbon fluid.

In each of these methods, the identifying steps involving a GC report can include monitoring the intensity value at one or more predetermined elution times.

In each of these methods, the spectroscopically analyzing steps can include conducting fluorescence spectroscopy, UV-Vis spectroscopy, Raman spectroscopy, near-infrared spectroscopy, chromatographic techniques, such as liquid chromatography-mass spectrometry (LC/MS), GLP (gel liquid permeation), or a combination thereof.

In each of these methods, the identifying steps involving a spectroscopic report can include comparing the spectroscopic report to a reference spectrum for the spectroscopic marker.

While it may be possible that the phthalein may be removed by unscrupulous persons, even under the most rigorous conditions, the pyrrolidinone is only partially removed providing absolute proof of the presence of the marker in the fuel/fluid sample.

Substantially all 1-alkyl pyrrolidinones will work well in these methods providing multiple combinations of phthalein and pyrrolidinone permitting greater flexibility of compositions chosen for an end user. For example, the pyrrolidinones may include, but are not limited to, 1-Methyl-2-pyrrolidinone, 1-Ethyl-2-pyrrolidinone, 1-Cyclohexyl-2-pyrrolidinone, 1-Octyl-2-pyrrolidinone, 1-Dodecyl-2-pyrrolidinone, ocyldecyl-2-pyrrolidinone, and 1-Vinyl-2-pyrrolidinone, or any other suitable pyrrolidinone, including, for example, all of the $C_1$ to $C_{16}$ alkyl pyrrolidinones.

The compositions according to embodiments of this disclosure may comprise from about 1 to about 99% spectroscopic marker, more preferably about 10 to about 60%, and even more preferably between about 15 to about 50%; about 1 to about 99% pyrrolidinone, more preferably between about 10 to about 80%, and even more preferably between about 20 to about 70%; from about 1 to about 99% solvent, more preferably about 10 to about 60%, and even more preferably between about 20 to about 50%. It is envisioned that in some embodiments of the disclosure, the composition will comprise at least one spectroscopic marker and a pyrrolidinone. The solvent may be of any suitable type, and is not limited to the use of solvent naphtha.

Figure 1:
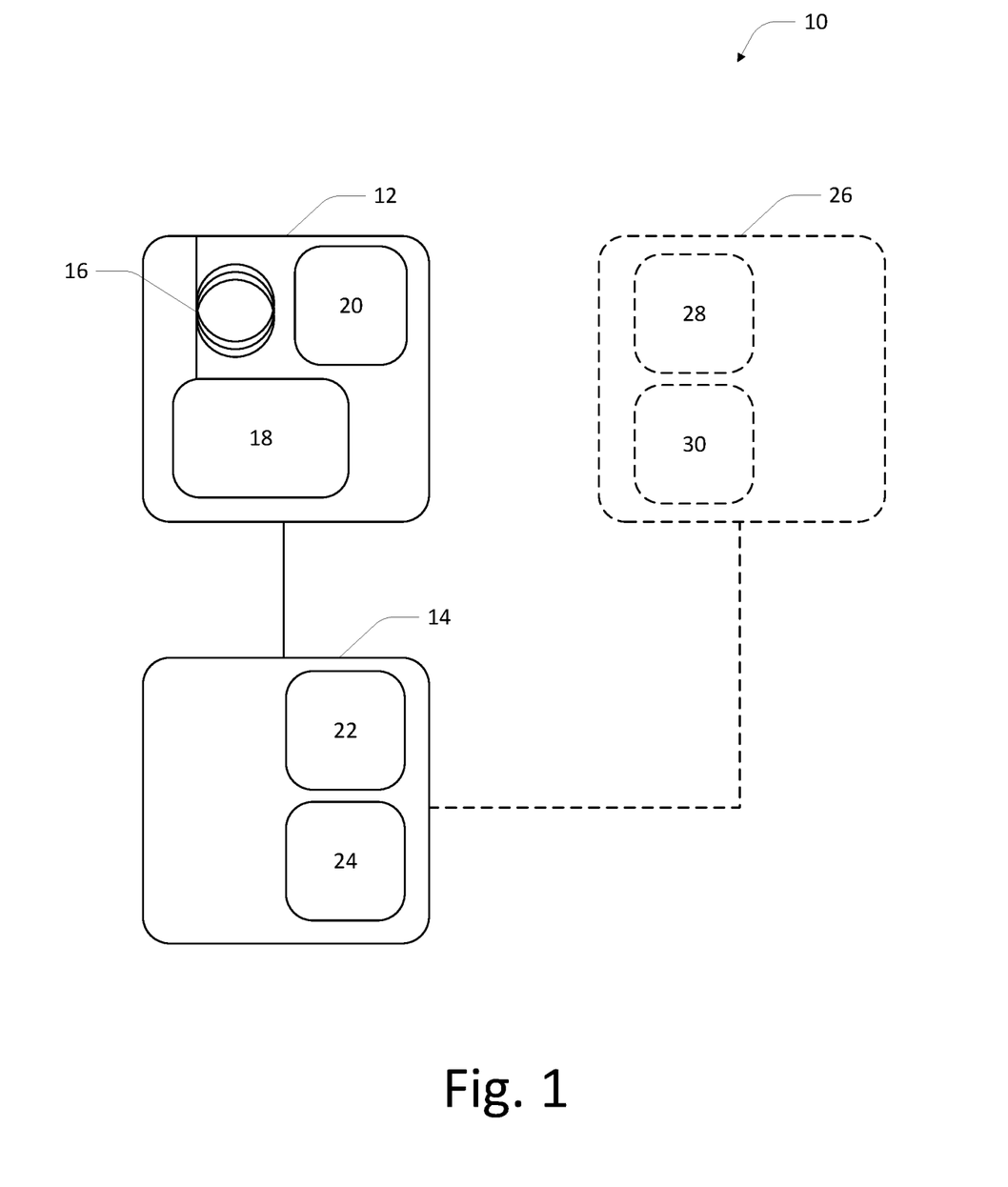
FIG. 1 is a system, in accordance with various aspects of the present disclosure.

Referring to FIG. 1, the present disclosure provides a system 10. The system can include a GC system 12 and a computer 14. The GC-NPD system 12 can include a GC column 16 and a GC detector 18. The GC system 12 can include a carrier gas source 20.

In some cases, the GC system 12 can be a GC-NPD system. In some cases, the GC system 12 can be a GC-MS system.

The GC column 16 can be a fused silica column, a polyethylene glycol column, a cyano propyl column, a trifluorpropyl column, a substituted polysiloxane column, or other column known those having ordinary skill in the chromatography arts to be suitable for separating the GC markers described herein from the hydrocarbon fluids. In some cases, the GC detector 18 can be a NPD. In some cases, the GC detector 18 can be a MS. In some cases, the GC detector 18 can be a NPD, including a FTD or an AFID, a MS, a HECD, a FID, an ECD, a PID, or a combination thereof. The nitrogen phosphorus detector can be a flame thermionic detector, an alkali flame-ionization detector, or other nitrogen phosphorus detectors known to those having ordinary skill in the chromatography arts. The carrier gas source 20 can be a helium source, a nitrogen source, or a combination thereof.

The computer 14 can include a processor 22 and a memory 24. The computer can also include various displays, inputs, and the like, as understood by those having ordinary skill in the computing arts. The memory can have stored thereon instructions that, when executed by the processor, cause the processor to receive GC reports and/or spectroscopy reports and execute the identify step or steps of any of the methods described herein.

The memory 24 can have stored thereon one or more reference GC reports, corresponding to GC markers or pyrrolidinones intended to be analyzed by the system 10.

The system 10 can further include a spectroscopy system 26. The spectroscopy system 26 can include a light source 28 and a light detector 30.

The memory 24 can have stored thereon one or more reference spectroscopic reports, corresponding to the spectroscopic markers intended to be analyzed by the system.

The GC system 12 and optional spectroscopy system 26 can have on-board processors and memories, as understood by those having ordinary skill in the art. Communication between the computer and the GC system 12 and optional spectroscopy system 26 can be wired or wireless, using any communication protocol known to those having ordinary skill in the communication arts.

Example 1. Experiments 1 to 24

In experiments 1 through 24, formulations were prepared with three different phthaleins, 4 different 1-alkylpyrrolidinones, and 2 different concentrations. Table 1 shows the formulations prepared. All formulations showed stable solutions, defined by no separation or precipitation, over 1 month, 3 month, and 6 month time periods.

TABLE 1

| Experiment (Formulation) number | Phthalein | Alkyl-Pyrrolidinone | Pyrrolidinone % | Stability 1 month | 3 months | 6 months |
|---|---|---|---|---|---|---|
| 1 | Cresolphthalein | Methyl | 30% | Stable | Stable | Stable |
| 2 | Cresolphthalein dibutyrate | Methyl | 30% | Stable | Stable | Stable |
| 3 | Thymolphthalein | Methyl | 30% | Stable | Stable | Stable |
| 4 | Cresolphthalein | Octyl | 30% | Stable | Stable | Stable |
| 5 | Cresolphthaein dibutyrate | Octyl | 30% | Stable | Stable | Stable |
| 6 | Thymolphthalein | Octyl | 30% | Stable | Stable | Stable |
| 7 | Cresolphthalein | dodecyl | 30% | Stable | Stable | Stable |
| 8 | Cresolphthalein dibutyrate | dodecyl | 30% | Stable | Stable | Stable |
| 9 | Thymolphthalein | dodecyl | 30% | Stable | Stable | Stable |
| 10 | Cresolphthalein | cyclohexyl | 30% | Stable | Stable | Stable |
| 11 | Cresolphthaein dibutyrate | cyclohexyl | 30% | Stable | Stable | Stable |
| 12 | Thymolphthalein | cyclohexyl | 30% | Stable | Stable | Stable |
| 13 | Cresolphthalein | Methyl | 60% | Stable | Stable | Stable |
| 14 | Cresolphthaein dibutyrate | Methyl | 60% | Stable | Stable | Stable |
| 15 | Thymolphthalein | Methyl | 60% | Stable | Stable | Stable |
| 16 | Cresolphthalein | Octyl | 60% | Stable | Stable | Stable |
| 17 | Cresolphthaein dibutyrate | Octyl | 60% | Stable | Stable | Stable |
| 18 | Thymolphthalein | Octyl | 60% | Stable | Stable | Stable |
| 19 | Creslphthalein | dodecyl | 60% | Stable | Stable | Stable |
| 20 | Cresolphthaein dibutyrate | dodecyl | 60% | Stable | Stable | Stable |
| 21 | Thymolphthalein | dodecyl | 60% | Stable | Stable | Stable |
| 22 | Cresolphthalein | cyclohexyl | 60% | Stable | Stable | Stable |
| 23 | Cresolphthaein dibutyrate | cyclohexyl | 60% | Stable | Stable | Stable |
| 24 | Thymolphthalein | cyclohexyl | 60% | Stable | Stable | Stable |

Example 2. Experiments 25 to 27

Calibration curves were prepared for three pyrrolidinones. Experiments 25, 26, and 27 were performed where standard concentrations of the pyrrolidinone at 1 ppm, 5 ppm, and 10 ppm. A 0.5 ppm point solution was also prepared for the 1-octyl-2-pyrrolidinone. Straight line calibration curves were obtained. Table 2 gives the area counts determined for the three experiments at each of the measured concentrations and the "$R^2$" or "R squared value" for each calibration curve. Reproducible retention times for the three-alkylpyrrolidinones were found to be 9.1 minutes, 10.0 minutes, and 15.1 minutes respectively for the 1-cyclohexyl, 1-octyl, and 1 dodecyl pyrrolidinones.

TABLE 2

| Experiment number | Identity | PPM 0.5 | 1 | 5 | 10 | R squared Value for best fit straight line |
|---|---|---|---|---|---|---|
| 25 | Calibration for 1-octyl-pyrrolidinone | 38000 | 81000 | 432000 | 934000 | 0.9988 |
| 26 | Calibration for 1-cyclohexyl-pyrrolidinone | | 126571 | 459429 | 843727 | 0.9995 |
| 27 | Calibration for 1-dodecyl-pyrrolidinone | | 109000 | 223000 | 393000 | 0.9976 |

GC conditions are described as follows (HP 6890 Series GC System)

Column: Capillary Column, Restek Rxi-1 ms, 30 m×0.5 µm×250 µl
Detector: Agilent 6890 Nitrogen Phosphorus Detector
Column Mode: Constant Flow, Splitless
Initial Temperature: 120° C.
Initial hold temperature: 0 min
Final Temperature: 250° C.
Ramp rate: 10° C./min
Hold time: 12 min
Injection Volume 1 µl

Example 3. Experiments 28 to 37

In experiments 28 thru 37, several of the formulations as indicated in Table 1, were prepared at a concentration of 20 ppm in Diesel fuel. The results of the experiments are tabulated in Table 3. Essentially identical retention times were found for the alkylpyrrolidinone. Excellent concentrations for the samples were obtained. 20 ppm samples as prepared should contain 6 ppm pyrrolidinone for those formulations with 30% pyrrolidinone in the formulations and 12 ppm for those formulations that have 60% pyrrolidinone.

TABLE 3

| Experiment number | Formulation from Table 1 | Retention time of major peak | Pyrolidinone concentration |
|---|---|---|---|
| 28 | 4 | 10.0 | 6 |
| 29 | 5 | 10.0 | 6 |
| 30 | 6 | 10.0 | 6 |
| 31 | 7 | 15.9 | 6 |
| 32 | 8 | 15.9 | 6 |
| 33 | 10 | 9.2 | 6 |
| 34 | 12 | 9.1 | 6 |
| 35 | 18 | 10.1 | 12 |
| 36 | 23 | 9.1 | 12 |
| 37 | 24 | 9.1 | 12 |

Example 4. Experiments 38 to 53

Laundering studies were performed on samples prepared in diesel fuel and in gasoline. For experiments 38 to 47, formulations as described in Table 1 were prepared at 10 and 20 ppm in gasoline and/or diesel fuel and subjected to column chromatography containing activated charcoal. The technique used was similar to one used in Asian Marketplaces where the removal of Fuel Markers is known to be a problem. In these experiments, 300 ml of marked fuel is subjected to a column (packed, internal diameter of 11 mm) containing 7.5 grams of activated charcoal (Darco®, 20-40 mesh, purchased from Aldrich, Cat #242268). Fuel was passed thru the column at about 1.5 ml per minute until approximately 300 ml of fuel was recovered from the column. The resultant solution was subjected to the same GC conditions described previously. Table 4 shows the results of Experiments 38 through 45, the results of the GC testing. It contains the percentage of pyrrolidinone remaining in the fuel after the above mentioned treatment with charcoal. It is worth noting that in both cases, gasoline showed better retention than the diesel fuel and in both cases the 20 ppm solutions showed better retention that the 10 ppm solutions.

Experiments 48 to 55 were done by performing classic caustic (4 parts diesel fuel solution plus 1 part 5% NaOH, shaken vigorously) and acid (5 parts diesel fuel plus 1 part 10% hydrochloric acid, shaken vigorously) washes on 20 ppm solutions of a variety of formulations. Tables 5 (caustic) and 6 (acid) show the amount of pyrrolidinone remaining after the laundering procedure. In the last column, the amount of phthalein detected in the washed sample is also shown. In all cases, the Charcoal and Caustic Wash removed much or all of the phthalein. For the HCl wash, essentially all the phthalein did remain, as expected. HCl is known to be a poor method for removing phthaleins from fuel.

TABLE 4

Charcoal laundering

| Exp. # | Fuel type | Conc. in ppm | Form. # | Pyrrolidinone | % GC marker remaining | Phthalein remaining |
|---|---|---|---|---|---|---|
| 38 | Gasoline | 10 | 5 | NOP | 52 | 0 |
| 39 | Gasoline | 20 | 5 | NOP | 41 | 0 |
| 40 | Diesel | 10 | 5 | NOP | 33 | 0 |
| 41 | Diesel | 20 | 5 | NOP | 67 | 0 |
| 42 | Diesel | 20 | 23 | NCP | 66 | 0 |
| 43 | Diesel | 20 | 20 | NDP | 79 | 0 |
| 44 | Diesel | 20 | 12 | NCP | 61% | 0 |
| 45 | Diesel | 20 | 6 | NOP | 57% | 0 |

TABLE 5

Caustic Laundering

| Exp. # | Fuel type | Conc. in ppm | Form. # | Pyrrolidinone | % GC marker remaining | Phthalein remaining |
|---|---|---|---|---|---|---|
| 46 | Diesel | 20 | 20 | NDP | 85% | 52 |
| 47 | Diesel | 20 | 12 | NCP | not run | 0 |
| 48 | Diesel | 20 | 6 | NOP | not run | 0 |
| 49 | Diesel | 20 | 8 | NDP | not run | 53 |

TABLE 6

Acid laundering

| Exp. # | Fuel type | Conc. in ppm | Form. # | Pyrrolidinone | % GC marker remaining | Phthalein remaining |
|---|---|---|---|---|---|---|
| 50 | Diesel | 20 | 8 | NDP | 100% | 100 |
| 51 | Diesel | 20 | 20 | NDP | 100% | 99.5 |
| 52 | Diesel | 20 | 6 | NOP | not run | 87 |
| 53 | Diesel | 20 | 12 | NCP | not run | 86 |

Example 5. Experiment 54

To verify the assignment of the retention times for the three pyrrolidinones used in the formulations 1 thru 24, Quadropole GC/MS was used. Using the same column and temperature conditions described for experiments 25 to 27, calibration standards were subjected to MS/GC detector [HP 5973 Mass Selective Detector]. For, 1-cyclohexylpyrrolidinone the M+ ion was found at 167 mu (Mass Units). For 1-octylpyrrolidinone the M+ ion was found at 197 mu. For the 1-dodecylpyrrolidinone, the M+ ion was found at 253 mu. These M+ ions are what is expected given the molecular weights of the pyrrolidinones.

The present disclosure also includes the following statements:

Statements

1. A method of identifying a hydrocarbon fluid containing a gas chromatography marker comprising a pyrrolidinone, the method comprising:

a) introducing a sample of the hydrocarbon fluid into a gas chromatography system, thereby resulting in a gas chromatography report of the sample; and b) identifying the presence of the pyrrolidinone in the hydrocarbon fluid using the gas chromatography report.

2. The method of statement 1, wherein the gas chromatography system is a gas chromatography with nitrogen phosphorus detector (GC-NPD) system and step a) is introducing the sample into the GC-NPD system.

3. The method of statement 2, wherein the GC-NPD system includes a flame thermionic detector or an alkali flame-ionization detector.

4. The method of statement 2 or 3, wherein the gas chromatography report resulting from step a) includes an intensity value that is proportional to an amount of nitrogen or phosphorus in the sample.

5. The method of statement 4, wherein the intensity is time-variable as a function of elution times of components of the sample.

6. The method of statement 5, wherein the identifying of step b) includes monitoring the intensity value at one or more predetermined elution times.

7. The method of statement 1, wherein the gas chromatography system is a gas chromatography-mass spectrometry (GC-MS) system, a gas chromatography-Hall electrolytic conductivity detector (GC-HECD) system, a gas chromatography-flame ionization detector (GC-FID) system, a gas chromatography-electron capture detector (GC-ECD) system, a gas chromatography-photoionization detector (GC-PID) system, or a combination thereof, and step a) is introducing the sample into the GC-MS system, the GC-HECD system, the GC-FID system, the GC-ECD system, the GC-PID system, or the combination thereof.

8. The method of any one of the preceding statements, wherein the gas chromatography system includes a fused silica column, a polyethylene glycol column, a cyano propyl column, a trifluorpropyl column, a substituted polysiloxane column, or a combination thereof and the introducing of step a) includes introducing the sample into the fused silica column, the polyethylene glycol column, the cyano propyl column, the trifluorpropyl column, the substituted polysiloxane column, or the combination thereof.

9. The method of any one of the preceding statements, wherein the introducing of step a) includes introducing the sample with a carrier gas selected from the group consisting of nitrogen, helium, and combinations thereof.

10. The method of any one of the preceding statements, wherein the identifying of step b) includes comparing the gas chromatography report to a reference report.

11. The method of any one of the preceding statements, wherein the pyrrolidinone is present in the hydrocarbon fluid in an amount of between 0.1 ppm and 500 ppm.

12. The method of any one of the preceding statements, the hydrocarbon fluid further comprising a spectroscopic marker, the method further comprising:
 c) spectroscopically analyzing a second sample of the hydrocarbon fluid, thereby resulting in a spectroscopic report of the second sample; and
 d) identifying the presence of the spectroscopic marker in the hydrocarbon fluid using the spectroscopic report.

13. The method of statement 12, wherein the spectroscopically analyzing of step c) includes conducting fluorescence spectroscopy, UV-Vis spectroscopy, Raman spectroscopy, near infrared spectroscopy, or a combination thereof.

14. The method of statement 12 or 13, wherein the identifying of step d) includes comparing the spectroscopic report to a reference spectrum.

15. The method of any one of statements 12 to the immediately preceding statement, wherein the spectroscopic marker is present in the hydrocarbon fluid in an amount of between 0.1 ppm and 500 ppm.

16. A method of marking a subset of hydrocarbon fluids in circulation within a market and detecting presence of the marking, the method comprising:
 a) adding a gas chromatography marker comprising a pyrrolidinone to the subset of the hydrocarbon fluids in circulation within the market;
 b) selecting a sample of one of the hydrocarbon fluids in circulation within the market;
 c) introducing at least a portion of the sample of one of the hydrocarbon fluids in circulation within the market into a gas chromatography system, thereby resulting in a gas chromatography report of the sample; and
 d) identifying the presence or absence of the pyrrolidinone in the sample using the gas chromatography report, thereby identifying whether the sample is from within or without the subset of hydrocarbon fluids.

17. The method of statement 16, wherein the gas chromatography system is a gas chromatography with nitrogen phosphorus detector (GC-NPD) system and step c) is introducing the sample into the GC-NPD system.

18. The method of statement 17, wherein the GC-NPD system includes a flame thermionic detector or an alkali flame-ionization detector.

19. The method of statement 17 or 18, wherein the gas chromatography report resulting from step c) includes an intensity value that is proportional to an amount of nitrogen or phosphorus in the sample.

20. The method of statement 19, wherein the intensity is time-variable as a function of elution times of components of the sample.

21. The method of statement 20, wherein the identifying of step d) includes monitoring the intensity value at one or more predetermined elution times.

22. The method of any one of statements 16 to the immediately preceding statement, wherein the gas chromatography system is a gas chromatography-mass spectrometry (GC-MS) system, a gas chromatography-Hall electrolytic conductivity detector (GC-HECD) system, a gas chromatography-flame ionization detector (GC-FID) system, a gas chromatography-electron capture detector (GC-ECD) system, a gas chromatography-photoionization detector (GC-PID) system, or a combination thereof, and step c) is introducing the sample into the GC-MS system, the GC-HECD system, the GC-FID system, the GC-ECD system, the GC-PID system, or the combination thereof.

23. The method of any one of statements 16 to the immediately preceding statement, wherein the gas chromatography system includes a fused silica column a polyethylene glycol column, a cyano propyl column, a trifluorpropyl column, a substituted polysiloxane column, or a combination thereof and the introducing of step c) includes introducing the sample into the fused silica column, the polyethylene glycol column, the cyano propyl column, the trifluorpropyl column, the substituted polysiloxane column, or the combination thereof.

24. The method of any one of statements 16 to the immediately preceding statement, wherein the introducing of step c) includes introducing the sample with a carrier gas selected from the group consisting of nitrogen, helium, and combinations thereof.

25. The method of any one of statements 16 to the immediately preceding statement, wherein the identifying of step d) includes comparing the gas chromatography report to a reference report.

26. The method of any one of statements 16 to the immediately preceding statement, wherein the adding of step a) includes adding the gas chromatography marker in an amount necessary to provide the pyrrolidinone in the subset of the hydrocarbon fluids in an amount of between 0.1 ppm and 500 ppm.

27. The method of any one of statements 16 to the immediately preceding statement, the method further comprising:
   e) adding a spectroscopic marker to the subset of the hydrocarbon fluids in circulation within the market;
   f) spectroscopically analyzing at least a second portion of the sample of one of the hydrocarbon fluids in circulation within the market, thereby resulting in a spectroscopic report of the sample; and
   g) identifying the presence or absence of the spectroscopic marker in the sample using the spectroscopic report, thereby identifying whether the sample is from within or without the subset of hydrocarbon fluids.

28. The method of statement 27, wherein the spectroscopically analyzing of step f) includes conducting fluorescence spectroscopy, UV-Vis spectroscopy, Raman spectroscopy, near infrared spectroscopy, or a combination thereof.

29. The method of statement 27 or 28, wherein the identifying of step g) includes comparing the spectroscopic report to a reference spectrum.

30. The method of any one of statements 27, wherein the adding of step e) includes adding the spectroscopic marker to the subset of the hydrocarbon fluids in an amount of between 0.1 ppm and 500 ppm.

31. A method of identifying marked hydrocarbon fluids that have been laundered, wherein unlaundered marked hydrocarbon fluids contain a gas chromatography marker and a spectroscopic marker, the gas chromatography marker including a pyrrolidinone, the method comprising:
   a) introducing a first portion of a hydrocarbon fluid sample that is suspecting of having been laundered into a gas chromatography system, thereby resulting in a gas chromatography report of the hydrocarbon fluid sample;
   b) spectroscopically analyzing a second portion of the hydrocarbon fluid sample, thereby resulting in a spectroscopic report of the hydrocarbon fluid sample;
   c) identifying the presence or absence of the gas chromatography marker using the gas chromatography report and identifying the presence or absence of the spectroscopic marker using the spectroscopic report; and
   d) based on the identifying of step c):
      if the gas chromatography marker and the spectroscopic marker are identified as present, then indicating that the hydrocarbon fluid sample is marked and unlaundered;
      if the gas chromatography marker is identified as present and the spectroscopic marker is identified as absent, then indicating that the hydrocarbon fluid sample is marked and laundered; and
      if the gas chromatography marker and the spectroscopic marker are identified as absent, then indicating the hydrocarbon fluid is unmarked.

32. The method of statement 31, wherein the gas chromatography system is a gas chromatography with nitrogen phosphorus detector (GC-NPD) system and step a) is introducing the first portion into the GC-NPD system.

33. The method of statement 32, wherein the GC-NPD system includes a flame thermionic detector or an alkali flame-ionization detector.

34. The method of statement 32 or 33, wherein the gas chromatography report resulting from step a) includes an intensity value that is proportional to an amount of nitrogen or phosphorus in the sample.

35. The method of statement 34, wherein the intensity is time-variable as a function of elution times of components of the sample.

36. The method of statement 35, wherein the identifying the presence or absence or the gas chromatography marker portion of step c) includes monitoring the intensity value at one or more predetermined elution times.

37. The method of any one of statements 31 to the immediately preceding statement, wherein the gas chromatography system is a gas chromatography-mass spectrometry (GC-MS) system, a gas chromatography-Hall electrolytic conductivity detector (GC-HECD) system, a gas chromatography-flame ionization detector (GC-FID) system, a gas chromatography-electron capture detector (GC-ECD) system, a gas chromatography-photoionization detector (GC-PID) system, or a combination thereof, and step a) is introducing the first portion into the GC-MS system, the GC-HECD system, the GC-FID system, the GC-ECD system, the GC-PID system, or the combination thereof.

38. The method of any one of statements 31 to the immediately preceding statement, wherein the gas chromatography system includes a fused silica column and the introducing of step a) includes introducing the sample into the fused silica column.

39. The method of any one of statements 31 to the immediately preceding statement, wherein the introducing of step a) includes introducing the sample with a carrier gas selected from the group consisting of nitrogen, helium, and combinations thereof.

40. The method of any one of statements 31 to the immediately preceding statement, wherein the identifying the presence or absence of the gas chromatography marker portion of step c) includes comparing the gas chromatography report to a reference report.

41. The method of any one of statements 31 to the immediately preceding statement, wherein the spectroscopically analyzing of step b) includes conducting fluorescence spectroscopy, UV-Vis spectroscopy, Raman spectroscopy, near infrared spectroscopy, or a combination thereof.

42. The method of any one of statements 31 to the immediately preceding statement, wherein the identifying the presence or absence of the spectroscopic marker portion of step c) includes comparing the spectroscopic report to a reference spectrum.

43. The method of any one of statements 12 to 15 and 27 to 42, wherein the spectroscopic marker is:

wherein $Ar^1$ and $Ar^2$ each independently represent a substituted or unsubstituted phenylene group or a substituted or unsubstituted naphthylene group; $R^1$ represents a straight or branched chain alkyl group having 1 to 22 carbon atoms; $R^2$ represents a hydrogen atom or a group of the formula $C(O)R^4$ where $R^4$ is a hydrogen atom or a straight or branched chain alkyl group having 1 to 22 carbon atoms; $R^3$ represents a hydrogen atom, a straight or branched chain alkyl group having 1 to 12 carbon atoms, a straight or branched chain alkoxy group having 1 to 12 carbon atoms, a hydroxyl group, a substituted or unsubstituted phenyl group or a substituted or unsubstituted naphthyl group; and Z represents a hydrogen atom or a group of atoms that combine with $Ar^2$ or $R^3$ to form a lactone ring.

44. The method of any one of statements 12 to 15 and 27 to 42, wherein the spectroscopic marker is a red dye or a yellow dye.

45. The method of statement 44, wherein the spectroscopic marker is Solvent Red 164 or Solvent Yellow 124.

46. The method of any one of statements 12 to 15 and 27 to 42, wherein the spectroscopic marker is a phthalein.

47. The method of any one of statements 12 to 15 and 27 to 42, wherein the spectroscopic marker is a phthalein dibutyrate.

48. The method of any one of statements 12 to 15 and 27 to 42, wherein the spectroscopic marker is a phthalein ester.

49. The method of any one of statements 12 to 15 and 27 to 42, wherein the spectroscopic marker is selected from the group consisting of fluoroscein dibutyrate, cresolphthalein, o-cresolphthalein dibutyrate, and thymolphthalein.

50. The method of any one of statements 12 to 15 and 27 to 42, wherein the spectroscopic marker is selected from the group consisting of cresolphthalein dibutyrate ester, cresolphthalein monobutyrate ester, cresolphthalein diisopropylate ester, cresolphthalein di-n-propylate ester, cresolphthalein dihexanoate ester, cresolphthalein dipentanoate ester, and cresolphthalein dilaurate ester.

51. The method of any one of statements 12 to 15 and 27 to 42, wherein the spectroscopic marker is selected from the group consisting of naphtholphthalein dibutyrate ester, thymolphthalein dibutyrate ester, and thymolphthalein dipropanoate ester.

52. The method of any one of statements 12 to 15 and 27 to 42, wherein the spectroscopic marker is selected from the group consisting of sec-butylphenolphthalein dibutyrate ester and di-sec-butylphenolphthalein dibutyrate ester.

53. The method of any one of the preceding statements, wherein the pyrrolidinone is a 1-alkyl-2-pyrrolidinone or a 1-alkenyl-2-pyrrolidinone.

54. The method of statement 53, wherein the pyrrolidinone is the 1-alkyl-2-pyrrolidinone.

55. The method of statement 54, the 1-alkyl-2-pyrrolidinone including a non-cyclic alkyl group having between 1 and 40 carbon atoms or a cycloalkyl group having between 4 and 40 atoms.

56. The method of statement 55, the non-cyclic alkyl group having between 3 and 24 carbon atoms, the cycloalkyl group having between 4 and 24 carbon atoms.

57. The method of statement 54, wherein the pyrrolidinone is selected from the group consisting of 1-methyl-2-pyrrolidinone, 1-ethyl-2-pyrrolidinone, 1-cyclohexyl-2-pyrrolidinone, 1-octyl-2-pyrrolidinone, 1-dodecyl-2-pyrrolidinone, and combinations thereof.

58. The method of statement 57, wherein the pyrrolidinone is 1-methyl-2-pyrrolidinone.

59. The method of statement 57, wherein the pyrrolidinone is 1-ethyl-2-pyrrolidinone.

60. The method of statement 57, wherein the pyrrolidinone is 1-cyclohexyl-2-pyrrolidinone.

61. The method of statement 57, wherein the pyrrolidinone is 1-octyl-2-pyrrolidinone.

62. The method of statement 57, wherein the pyrrolidinone is 1-dodecyl-2-pyrrolidinone.

63. The method of statement 53, wherein the pyrrolidinone is the 1-alkenyl-2-pyrrolidinone.

64. The method of statement 63, wherein the 1-alkenyl-2-pyrrolidinone includes an alkenyl group having between 2 carbon atoms and 40 carbon atoms.

65. The method of statement 64, the alkenyl group having between 2 carbon atoms and 24 carbon atoms.

66. The method of statement 63, wherein the pyrrolidinone is 1-vinyl-2-pyrrolidinone.

67. A marker composition comprising:
a gas chromatography marker comprising a pyrrolidinone; and
a solvent,
wherein the pyrrolidinone is a 1-alkyl-2-pyrrolidinone or a 1-alkenyl-2-pyrrolidinone, the 1-alkyl-2-pyrrolidinone including a non-cyclic alkyl group having between 3 and 7 carbon atoms, between 9 and 11 carbon atoms, or between 13 and 24 carbon atoms or a cycloalkyl group having between 4 and 24 carbon atoms, the 1-alkenyl-2-pyrrolidinone including an alkenyl group having between 2 and 24 carbon atoms.

68. The marker composition of statement 67, wherein the gas chromatography marker is present in an amount by weight of between 1% and 99% and the solvent is present in an amount by weight of between 1% and 99%.

69. The marker composition of statement 67, wherein the gas chromatography marker is present in an amount by weight of between 25% and 75% and the solvent is present in an amount by weight of between 25% and 75%.

70. The marker composition of statement 67, wherein the gas chromatography marker is present in an amount by weight of between 40% and 60% and the solvent is present in an amount by weight of between 40% and 60%.

71. The marker composition of statement 67, the marker composition consisting essentially of the gas chromatography marker and the solvent.

72. The marker composition of statement 71, wherein the gas chromatography marker is present in an amount by weight of between 1% and 99% and the solvent is present in an amount by weight of between 1% and 99%.

73. The marker composition of statement 71, wherein the gas chromatography marker is present in an amount by weight of between 25% and 75% and the solvent is present in an amount by weight of between 25% and 75%.

74. The marker composition of statement 71, wherein the gas chromatography marker is present in an amount by weight of between 40% and 60% and the solvent is present in an amount by weight of between 40% and 60%.

75. The marker composition of statement 67, the marker composition consisting of the gas chromatography marker and the solvent.

76. The marker composition of statement 75, wherein the gas chromatography marker is present in an amount by weight of between 1% and 99% and the solvent is present in an amount by weight of between 1% and 99%.

77. The marker composition of statement 75, wherein the gas chromatography marker is present in an amount by weight of between 25% and 75% and the solvent is present in an amount by weight of between 25% and 75%.

78. The marker composition of statement 75, wherein the gas chromatography marker is present in an amount by weight of between 40% and 60% and the solvent is present in an amount by weight of between 40% and 60%.

79. The marker composition of statement 67, the marker composition further comprising a spectroscopic marker.

80. The marker composition of statement 79, wherein the gas chromatography marker is present in an amount by weight of between 10% and 85%, the spectroscopic marker is present in an amount by weight of between 5% and 80%, and the solvent is present in an amount by weight of between 10% and 85%.

81. The marker composition of statement 79, wherein the gas chromatography marker is present in an amount by weight of between 20% and 70%, the spectroscopic marker is present in an amount by weight of between 10% and 50%, and the solvent is present in an amount by weight of between 20% and 70%.

82. The marker composition of statement 79, wherein the gas chromatography marker is present in an amount by weight of between 25% and 60%, the spectroscopic marker is present in an amount by weight of between 15% and 25%, and the solvent is present in an amount by weight of between 25% and 60%.

83. The marker composition of statement 79, the marker composition consisting essentially of the gas chromatography marker, the spectroscopic marker, and the solvent.

84. The marker composition of statement 80, wherein the gas chromatography marker is present in an amount by weight of between 10% and 85%, the spectroscopic marker is present in an amount by weight of between 5% and 80%, and the solvent is present in an amount by weight of between 10% and 85%.

85. The marker composition of statement 80, wherein the gas chromatography marker is present in an amount by weight of between 20% and 70%, the spectroscopic marker is present in an amount by weight of between 10% and 50%, and the solvent is present in an amount by weight of between 20% and 70%.

86. The marker composition of statement 80, wherein the gas chromatography marker is present in an amount by weight of between 25% and 60%, the spectroscopic marker is present in an amount by weight of between 15% and 25%, and the solvent is present in an amount by weight of between 25% and 60%.

87. The marker composition of statement 79, the marker composition consisting of the gas chromatography marker, the spectroscopic marker, and the solvent.

88. The marker composition of statement 87, wherein the gas chromatography marker is present in an amount by weight of between 10% and 85%, the spectroscopic marker is present in an amount by weight of between 5% and 80%, and the solvent is present in an amount by weight of between 10% and 85%.

89. The marker composition of statement 87, wherein the gas chromatography marker is present in an amount by weight of between 20% and 70%, the spectroscopic marker is present in an amount by weight of between 10% and 50%, and the solvent is present in an amount by weight of between 20% and 70%.

90. The marker composition of statement 87, wherein the gas chromatography marker is present in an amount by weight of between 25% and 60%, the spectroscopic marker is present in an amount by weight of between 15% and 25%, and the solvent is present in an amount by weight of between 25% and 60%.

91. The marker composition of any one of statements 67 to 90, wherein the solvent is selected from the group consisting of petroleum naphtha, an alcohol, a glycol ether, dimethyl formamide, dimethyl sulfoxide, xylene, toluene, acetone, ethyl acetate, a petroleum product, and combinations thereof.

92. The marker composition of any one of statements 67 to 90, wherein the solvent is a mixture of petroleum napthta and fuel additives.

93. A marker composition comprising:
a gas chromatography marker comprising a pyrrolidinone; and
a spectroscopic marker,
wherein the pyrrolidinone is a 1-alkyl-2-pyrrolidinone or a 1-alkenyl-2-pyrrolidinone, the 1-alkyl-2-pyrrolidinone including a non-cyclic alkyl group having between 3 and 7 carbon atoms, between 9 and 11 carbon atoms, or between 13 and 24 carbon atoms or a cycloalkyl group having between 4 and 24 carbon atoms, the 1-alkenyl-2-pyrrolidinone including an alkenyl group having between 2 and 24 carbon atoms.

94. The marker composition of statement 93, wherein the gas chromatography marker is present in an amount by weight of between 1% and 99% and the spectroscopic marker is present in an amount by weight of between 1% and 99%.

95. The marker composition of statement 93, wherein the gas chromatography marker is present in an amount by weight of between 25% and 75% and the spectroscopic marker is present in an amount by weight of between 25% and 75%.

96. The marker composition of statement 93, wherein the gas chromatography marker is present in an amount by weight of between 40% and 60% and the spectroscopic marker is present in an amount by weight of between 40% and 60%.

97. The marker composition of statement 93, the marker composition consisting essentially of the gas chromatography marker and the spectroscopic marker.

98. The marker composition of statement 97, wherein the gas chromatography marker is present in an amount by weight of between 1% and 99% and the spectroscopic marker is present in an amount by weight of between 1% and 99%.

99. The marker composition of statement 97, wherein the gas chromatography marker is present in an amount by weight of between 25% and 75% and the spectroscopic marker is present in an amount by weight of between 25% and 75%.

100. The marker composition of statement 97, wherein the gas chromatography marker is present in an amount by weight of between 40% and 60% and the spectroscopic marker is present in an amount by weight of between 40% and 60%.

101. The marker composition of statement 93, the marker composition consisting of the gas chromatography marker and the spectroscopic marker.

102. The marker composition of statement 101, wherein the gas chromatography marker is present in an amount by weight of between 1% and 99% and the spectroscopic marker is present in an amount by weight of between 1% and 99%.

103. The marker composition of statement 101, wherein the gas chromatography marker is present in an amount by weight of between 25% and 75% and the spectroscopic marker is present in an amount by weight of between 25% and 75%.

104. The marker composition of statement 101, wherein the gas chromatography marker is present in an amount by weight of between 40% and 60% and the spectroscopic marker is present in an amount by weight of between 40% and 60%.

105. The marker composition of any one of statements 67 to the immediately preceding statement, wherein the marker composition is nonaqueous.

106. The marker composition of any one of statements 67 to the immediately preceding statement, wherein adding the marker composition to a hydrocarbon fluid in an amount of 500 ppm of the pyrrolidinone results in a marked hydrocarbon fluid that, when introduced to a gas chromatography system, produces a gas chromatography signal that is distinguishable from a reference gas chromatography signal for an unmarked hydrocarbon fluid.

107. The marker composition of any one of statements 67 to the immediately preceding statement, wherein adding the marker composition to a hydrocarbon fluid in an amount of 50 ppm of the pyrrolidinone results in a marked hydrocarbon fluid that, when introduced to a gas chromatography system, produces a gas chromatography signal that is distinguishable from a reference gas chromatography signal for an unmarked hydrocarbon fluid.

108. The marker composition of any one of statements 67 to the immediately preceding statement, wherein adding the marker composition to a hydrocarbon fluid in an amount of 5 ppm of the pyrrolidinone results in a marked hydrocarbon fluid that, when introduced to a gas chromatography system, produces a gas chromatography signal that is distinguishable from a reference gas chromatography signal for an unmarked hydrocarbon fluid.

109. The marker composition of any one of statements 106 to 108, wherein the gas chromatography system is a gas chromatography with nitrogen phosphorus detector system and the gas chromatography signal is a gas chromatography with nitrogen phosphorus detector signal.

110. The marker composition of any one of statements 67 to the immediately preceding statement, wherein the gas chromatography marker consists essentially of the pyrrolidinone.

111. The marker composition of any one of statements 67 to the immediately preceding statement, wherein the gas chromatography marker consists of the pyrrolidinone.

112. The marker composition of any one of statements 67 to statement 111, wherein the pyrrolidinone is the 1-alkyl-2-pyrrolidinone.

113. The marker composition of statement 112, the 1-alkyl-2-pyrrolidinone including the non-cyclic alkyl group having between 3 and 7 carbon atoms.

114. The marker composition of statement 112, the 1-alkyl-2-pyrrolidinone including the non-cyclic alkyl group having between 9 and 11 carbon atoms.

115. The marker composition of statement 112, the 1-alkyl-2-pyrrolidinone including the non-cyclic alkyl group having between 13 and 24 carbon atoms.

116. The marker composition of statement 115, wherein the pyrrolidinone is 1-octadecyl-2-pyrrolidinone.

117. The marker composition of statement 112, the 1-alkyl-2-pyrrolidinone including the cycloalkyl group having between 4 and 24 carbon atoms.

118. The marker composition of statement 117, wherein the 1-alkyl-2-pyrrlidinone is 1-cyclohexyl-2-pyrrolidinone.

119. The marker composition of any one of statements 67 to statement 111, wherein the pyrrolidinone is the 1-alkenyl-2-pyrrolidinone.

120. The marker composition of statement 119, wherein the pyrrolidinone is 1-vinyl-2-pyrrolidinone.

121. The marker composition of any one of statements 79 to 120, wherein the spectroscopic marker is:

wherein $Ar^1$ and $Ar^2$ each independently represent a substituted or unsubstituted phenylene group or a substituted or unsubstituted naphthylene group; $R^1$ represents a straight or branched chain alkyl group having 1 to 22 carbon atoms; $R^2$ represents a hydrogen atom or a group of the formula $C(O)R^4$ where $R^4$ is a hydrogen atom or a straight or branched chain alkyl group having 1 to 22 carbon atoms; $R^3$ represents a hydrogen atom, a straight or branched chain alkyl group having 1 to 12 carbon atoms, a straight or branched chain alkoxy group having 1 to 12 carbon atoms, a hydroxyl group, a substituted or unsubstituted phenyl group or a substituted or unsubstituted naphthyl group; and Z represents a hydrogen atom or a group of atoms that combine with $Ar^2$ or $R^3$ to form a lactone ring.

122. The marker composition of any one of statements 79 to 120, wherein the spectroscopic marker is a red dye or a yellow dye.

123. The marker composition of statement 122, wherein the spectroscopic marker is Solvent Red 164 or Solvent Yellow 124.

124. The marker composition of any one of statements 79 to 120, wherein the spectroscopic marker is a phthalein.

125. The marker composition of any one of statements 79 to 120, wherein the spectroscopic marker is a phthalein dibutyrate.

126. The marker composition of any one of statements 79 to 120, wherein the spectroscopic marker is a phthalein ester.

127. The marker composition of any one of statements 79 to 120, wherein the spectroscopic marker is selected from the group consisting of fluoroscein dibutyrate, cresolphthalein, o-cresolphthalein dibutyrate, and thymolphthalein.

128. The marker composition of any one of statements 79 to 120, wherein the spectroscopic marker is selected from the group consisting of cresolphthalein dibutyrate ester, cresolphthalein monobutyrate ester, cresolphthalein diisopropylate ester, cresolphthalein di-n-propylate ester, cresolphthalein dihexanoate ester, cresolphthalein dipentanoate ester, and cresolphthalein dilaurate ester.

129. The marker composition of any one of statements 79 to 120, wherein the spectroscopic marker is selected from the group consisting of naphtholphthalein dibutyrate ester, thymolphthalein dibutyrate ester, and thymolphthalein dipropanoate ester.

130. The marker composition of any one of statements 79 to 120, wherein the spectroscopic marker is selected from the group consisting of sec-butylphenolphthalein dibutyrate ester and di-sec-butylphenolphthalein dibutyrate ester.

131. A marked hydrocarbon fluid comprising:
 a hydrocarbon fluid;
 the marker composition of any one of statements 67 to 130 in an amount sufficient to provide a concentration of the pyrrolidinone in the marked hydrocarbon fluid of between 0.1 ppm and 500 ppm.

132. A marked hydrocarbon fluid consisting essentially of:
 a hydrocarbon fluid;
 the marker composition of any one of statements 67 to 130 in an amount sufficient to provide a concentration of the pyrrolidinone in the marked hydrocarbon fluid of between 0.1 ppm and 500 ppm.

133. A marked hydrocarbon fluid consisting of:
 a hydrocarbon fluid;
 the marker composition of any one of statements 67 to 130 in an amount sufficient to provide a concentration of the pyrrolidinone in the marked hydrocarbon fluid of between 0.1 ppm and 500 ppm.

134. A marked hydrocarbon fluid comprising:
 a hydrocarbon fluid;
 the marker composition of any one of statements 79 to 130 in an amount sufficient to provide a concentration of the spectroscopic marker in the marked hydrocarbon fluid of between 0.1 ppm and 500 ppm.

135. A marked hydrocarbon fluid consisting essentially of:
   a hydrocarbon fluid;
   the marker composition of any one of statements 79 to 130 in an amount sufficient to provide a concentration of the spectroscopic marker in the marked hydrocarbon fluid of between 0.1 ppm and 500 ppm.

136. A marked hydrocarbon fluid consisting of:
   a hydrocarbon fluid;
   the marker composition of any one of statements 79 to 130 in an amount sufficient to provide a concentration of the spectroscopic marker in the marked hydrocarbon fluid of between 0.1 ppm and 500 ppm.

137. The marked hydrocarbon fluid of any one of statements 131 to 136, wherein the hydrocarbon fluid is selected from the group consisting of a petroleum-derived liquid hydrocarbon, gasoline, gasohol, diesel fuel, a petroleum-derived solvent, a petroleum-derived lubricant, a hydraulic fluid, kerosene, jet fuel, heating oil, bunker fuel, and combinations thereof.

138. A kit comprising:
   the marker composition of any one of statements 67 to 130; and
   a reference gas chromatography report for the pyrrolidinone.

139. A kit comprising:
   the marker composition of any one of statements 79 to 130; and
   a reference spectroscopic report for the spectroscopic marker.

140. A system for identifying hydrocarbon fluids marked with a gas chromatography marker including a pyrrolidinone, the system comprising:
   a gas chromatography with nitrogen phosphorus detector (GC-NPD) system; and
   a computer having a processor and a memory, the memory having stored thereon a reference gas chromatography report for the pyrrolidinone and instructions that, when executed by the processor, cause the processor to receive a gas chromatography report from the GC-NPD system and identify the presence or absence of the gas chromatography marker based on a comparison with the reference gas chromatography report.

141. The system of statement 140, the GC-NPD system comprising a flame thermionic detector of an alkali flame-ionization detector.

142. The system of statement 140 or 141, the GC-NPD system comprising a fused silica gas chromatography column.

143. The system of any one of statements 140 to 142, the GC-NPD system further comprising a carrier gas source configured to deliver nitrogen or helium as a carrier gas.

144. The system of any one of statements 140 to 143, the hydrocarbon fluids further marked with a spectroscopic marker, the system further comprising: a spectroscopy system.

145. The system of statement 144, the memory having stored thereon a reference spectroscopy report for the spectroscopic marker and instructions that, when executed by the processor, cause the processor to receive a spectroscopy report from the spectroscopy system and identify the presence or absence of the spectroscopic marker based on a comparison with the reference spectroscopy report.

146. The system of statement 144 or 145, wherein the spectroscopy system is a fluorescence spectroscopy system, a UV-Vis spectroscopy system, or a Raman spectroscopy system.

The present invention has been described in terms of one or more preferred embodiments, and it should be appreciated that many equivalents, alternatives, variations, and modifications, aside from those expressly stated, are possible and within the scope of the invention.

The invention claimed is:
1. A method comprising:
   a) adding between 0.1 ppm and 500 ppm of a gas chromatography marker to a hydrocarbon fluid, the gas chromatography marker comprising a pyrrolidinone, wherein the pyrrolidinone is selected from the group consisting of 1-alkenyl-2-pyrrolidinone, 1-alkyl-2-pyrrolidinone wherein the alkyl group has 3 or more carbon atoms, 1-vinyl-2-pyrrolidinone, 1-ethyl-2-pyrrolidinone, 1-cyclohexyl-2-pyrrolidinone, 1-octyl-2-pyrrolidinone, 1-dodecyl-2-pyrrolidinone, and combinations thereof;
   b) introducing a portion of the hydrocarbon fluid containing the gas chromatography marker into a gas chromatography system, thereby resulting in a gas chromatography report; and
   c) identifying presence of the pyrrolidinone in the hydrocarbon fluid using the gas chromatography report.

2. The method of claim 1, wherein the pyrrolidinone is 1-alkenyl-2-pyrrolidinone.

3. The method of claim 1, wherein the pyrrolidinone is 1-alkyl-2-pyrrolidinone, wherein the alkyl group has 3 or more carbon atoms.

4. The method of claim 1, wherein the pyrrolidinone is 1-vinyl-2-pyrrolidinone.

5. The method of claim 3, wherein the pyrrolidinone is selected from the group consisting of 1 ethyl-2-pyrrolidinone, 1-cyclohexyl-2-pyrrolidinone, 1-octyl-2-pyrrolidinone, 1-dodecyl-2-pyrrolidinone, and combinations thereof.

6. The method of claim 5, wherein the pyrrolidinone is 1-ethyl-2-pyrrolidinone.

7. The method of claim 5, wherein the pyrrolidinone is 1-cyclohexyl-2-pyrrolidinone.

8. The method of claim 5, wherein the pyrrolidinone is 1-octyl-2-pyrrolidinone.

9. The method of claim 5, wherein the pyrrolidinone is 1-dodecyl-2-pyrrolidinone.

10. A method of identifying a hydrocarbon fluid containing a gas chromatography marker comprising a pyrrolidinone, the method comprising:
   a) introducing a sample of the hydrocarbon fluid into a gas chromatography system, thereby resulting in a gas chromatography report of the sample; and
   b) identifying presence of the pyrrolidinone in the hydrocarbon fluid using the gas chromatography report, wherein the pyrrolidinone is selected from the group consisting of 1-alkenyl-2-pyrrolidinone, 1-alkyl-2-pyrrolidinone wherein the alkyl group has 3 or more carbon atoms, 1-vinyl-2-pyrrolidinone, 1-ethyl-2-pyrrolidinone, 1-cyclohexyl-2-pyrrolidinone, 1-octyl-2-pyrrolidinone, 1-dodecyl-2-pyrrolidinone, and combinations thereof.

11. The method of claim 10, wherein the pyrrolidinone is 1-alkenyl-2-pyrrolidinone.

12. The method of claim 10, wherein the pyrrolidinone is 1-alkyl-2-pyrrolidinone wherein the alkyl group has 3 or more carbon atoms.

13. The method of claim 10, wherein the pyrrolidinone is 1-vinyl-2-pyrrolidinone.

14. A method of identifying a hydrocarbon fluid containing a gas chromatography marker comprising a pyrrolidinone, the method comprising:
   a) introducing a sample of the hydrocarbon fluid into a gas chromatography system, thereby resulting in a gas chromatography report of the sample; and
   b) identifying presence of the pyrrolidinone in the hydrocarbon fluid using the gas chromatography report, wherein the pyrrolidinone is 1-alkenyl-2-pyrrolidinone.

15. The method of claim 14, wherein the pyrrolidinone is 1-vinyl-2-pyrrolidinone.

16. A method of identifying a hydrocarbon fluid containing a gas chromatography marker comprising a pyrrolidinone, the method comprising:
   a) introducing a sample of the hydrocarbon fluid into a gas chromatography system, thereby resulting in a gas chromatography report of the sample; and
   b) identifying presence of the pyrrolidinone in the hydrocarbon fluid using the gas chromatography report, wherein the pyrrolidinone is 1-vinyl-2-pyrrolidinone.

\* \* \* \* \*

UNITED STATES PATENT AND TRADEMARK OFFICE
CERTIFICATE OF CORRECTION

PATENT NO. : 11,385,218 B2
APPLICATION NO. : 16/683425
DATED : July 12, 2022
INVENTOR(S) : Michael P. Hinton et al.

It is certified that error appears in the above-identified patent and that said Letters Patent is hereby corrected as shown below:

In the Specification

Column 8, Line 19, "pyrolines" should be --pyrazines--.

Signed and Sealed this
Twenty-second Day of August, 2023

Katherine Kelly Vidal
*Director of the United States Patent and Trademark Office*